(12) United States Patent
Fan

(10) Patent No.: US 8,226,255 B2
(45) Date of Patent: Jul. 24, 2012

(54) KEY BUTTON WITH ANTI-BACTERIAL LIGHT SOURCE

(75) Inventor: Chao-Tsung Fan, Taipei Hsien (TW)

(73) Assignee: Hon Hai Precision Industry Co., Ltd., Tu-Cheng, New Taipei (TW)

(*) Notice: Subject to any disclaimer, the term of this patent is extended or adjusted under 35 U.S.C. 154(b) by 302 days.

(21) Appl. No.: 12/628,227

(22) Filed: Dec. 1, 2009

(65) Prior Publication Data
US 2011/0100790 A1    May 5, 2011

(30) Foreign Application Priority Data

Oct. 30, 2009   (CN) .......................... 2009 1 0309093

(51) Int. Cl.
*F21V 33/00* (2006.01)
*F21V 11/16* (2006.01)
*H01J 37/20* (2006.01)
*H01J 13/04* (2006.01)

(52) U.S. Cl. ............... 362/95; 362/240; 250/455.11; 200/333; 200/313

(58) Field of Classification Search .......... 362/612, 362/555, 559, 84, 95, 230, 236, 240, 249.02, 362/311.02; 250/455.11, 461.1; 200/333, 200/341, 345, 313, 314, 317
See application file for complete search history.

(56) References Cited

U.S. PATENT DOCUMENTS

| | | | | |
|---|---|---|---|---|
| 3,272,927 A | * | 9/1966 | Peebles | 379/452 |
| 3,314,746 A | * | 4/1967 | Millar | 250/504 R |
| 3,619,591 A | * | 11/1971 | Korski | 200/314 |
| 3,755,661 A | * | 8/1973 | Bouvrande | 362/253 |
| 4,163,883 A | * | 8/1979 | Boulanger | 200/314 |
| 4,225,766 A | * | 9/1980 | Pfeifer et al. | 200/314 |
| 4,710,634 A | * | 12/1987 | Brookes | 250/455.11 |
| 4,749,832 A | * | 6/1988 | Schlosser | 200/314 |
| 4,758,701 A | * | 7/1988 | Nagel | 200/314 |
| 4,771,725 A | * | 9/1988 | Miyaguchi et al. | 200/314 |
| 4,778,966 A | * | 10/1988 | Obata et al. | 200/314 |
| 5,266,949 A | * | 11/1993 | Rossi | 341/22 |
| 5,280,145 A | * | 1/1994 | Mosier et al. | 200/313 |

* cited by examiner

*Primary Examiner* — Ismael Negron
(74) *Attorney, Agent, or Firm* — Altis Law Group, Inc.

(57) ABSTRACT

A button includes a keycap made of transparent material and including a first side surface and a second side surface opposite to the first side surface, a light guide block set on the first side surface of the keycap, and an ultraviolet lighting element set on the first side surface to emit ultraviolet light. Ultraviolet light emitted by the ultraviolet lighting element may enter into the light guide block, then is reflected by the light guide block to pass through the keycap to arrive to the second side surface of the keycap.

5 Claims, 3 Drawing Sheets

KEY BUTTON WITH ANTI-BACTERIAL LIGHT SOURCE

BACKGROUND

1. Technical Field

The present disclosure relates to a button.

2. Description of Related Art

Push buttons are often employed in public places, such as for controlling elevators, for operating game equipment, etc. These buttons are touched frequently by many, therefore, they can be contaminated by many kinds of bacteria, which will become a health hazard.

DETAILED DESCRIPTION

Figure 1:
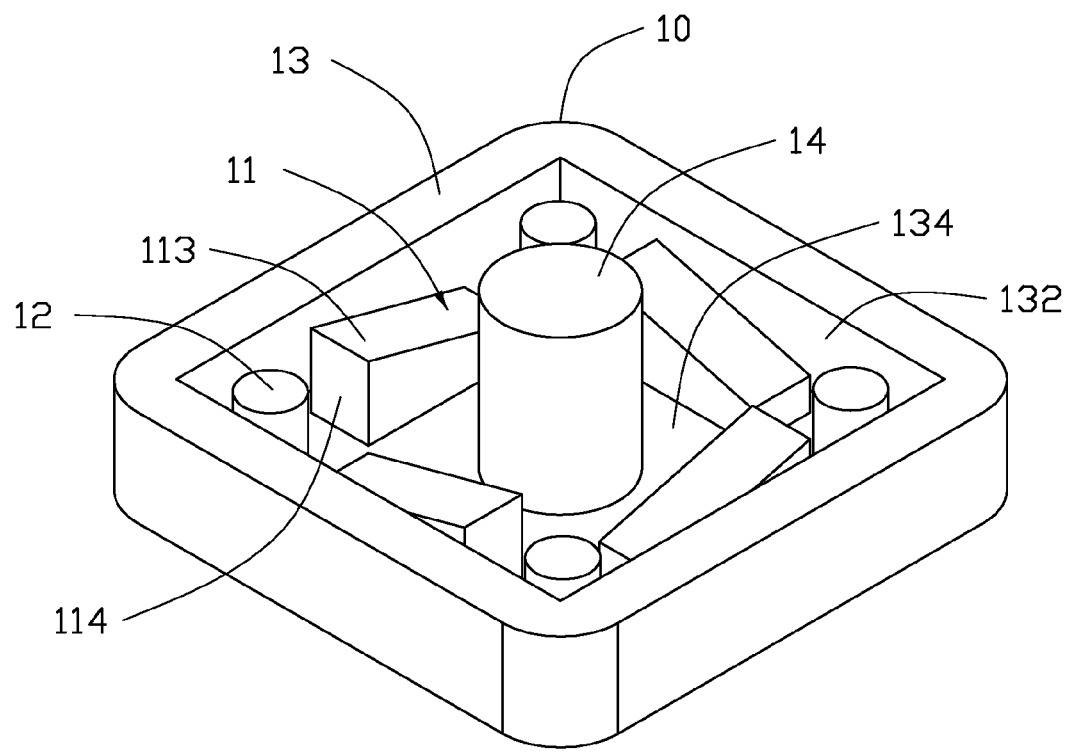
FIG. 1 is an isometric view of an exemplary embodiment of a button.
Figure 2:
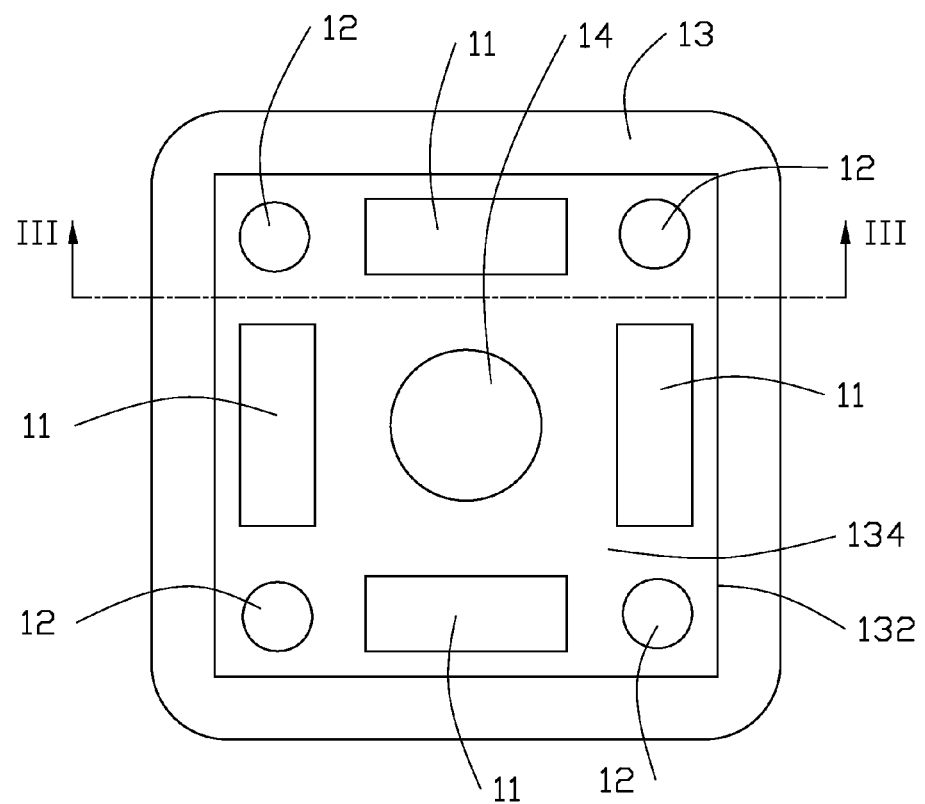
FIG. 2 is a top plan view of the button of FIG. 1.
Figure 3:
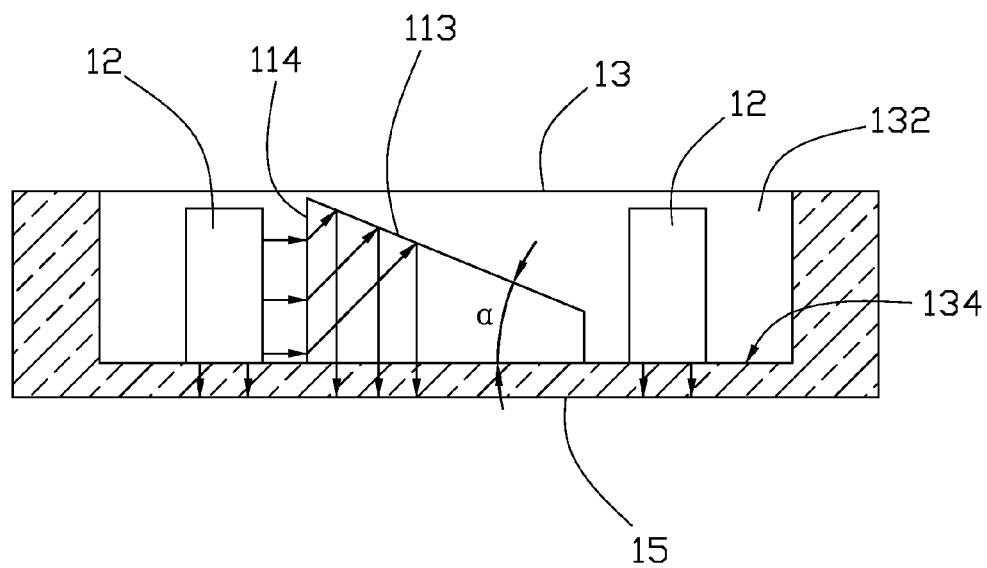
FIG. 3 is a cross-sectional view of FIG. 2, taken along the line III-III.

Referring to FIG. 1 to FIG. 3, an exemplary embodiment of a button includes a quadrate-shaped keycap 10. A depressed portion 132 is defined in a first side surface 13 of the keycap 10. Four light guide blocks 11, four column-shaped ultraviolet light-emitting diodes (LEDs) 12, and a column-shaped pressing bar 14 are set on a bottom 134 of the depressed portion 132. The keycap 10 is made of transparent material, such as acrylic resin.

The ultraviolet LEDs 12 are separately adhered on four corners of the bottom 134 of the depressed portion 132. The ultraviolet LEDs 12 may be powered by an external circuit. In another embodiment, the ultraviolet LEDs 12 may be replaced by other types of ultraviolet lighting elements.

Each light guide block 11 is generally trapezoid-shaped, and is made of transparent material, such as acrylic resin. In one embodiment, the light guide blocks 11 are integrally formed with the keycap 10. Each light guide block 11 is arranged between two adjacent ultraviolet LEDs 12. An angle α is formed between a top surface 113 of each light guide block 11 and the bottom 134 of the depressed portion 132. A height of each light guide block 11 is gradually decreased from a corresponding ultraviolet LED 12 to an adjacent ultraviolet LED 12. Four sidewalls 114 extend from sides of the top surface 113 of the light guide block 11, and are vertically connected to the bottom 134 of the depressed portion 132. The sidewall 114 of each light guide block 11 at the taller end of the light guide block 11 is used to allow ultraviolet light emitted by a corresponding ultraviolet LED 12 to enter into the light guide block 11. Surfaces of the light guide blocks 11 are processed for reflecting ultraviolet light by known technology.

The pressing bar 14 is set on a center of the bottom 134 of the depressed portion 132, surrounded by the light guide blocks 11 and the ultraviolet LEDs 12. The pressing bar 14 functions as a triggering portion to turn on or turn off an electronic switch adjacent to the button, to control an electronic device.

In use, the ultraviolet LEDs 12 are powered on by the external circuit and start emitting ultraviolet light. A first part of the ultraviolet light enters into the light guide blocks 11 through the sidewalls 114 at the taller ends of the light guide blocks 11, then is reflected by the top surfaces 113 to a second side surface 15 of the keycap 10 opposite to the first side surface 13 of the keycap 10, to kill the bacteria on the second side surface 15 of the keycap 10. A second part of the ultraviolet light is directly transmitted to the second side surface 15 of the keycap 10 through the bottom 134 of the depressed portion 132.

The light path arrows in FIG. 3 just help to explain the direction of ultraviolet light transmission for illustration purpose only, and should not be interpreted as showing a specific angle required by the ultraviolet light entering into the sidewalls 114.

In other embodiments, numbers, shapes, and placement of the light guide blocks 11 and the ultraviolet LEDs 12 can be regulated corresponding to need. The depressed portion 132 may not be needed, while the light guide blocks 11, the ultraviolet LEDs 12, and the pressing bar 14 may be directly set on the first side surface 13 of the keycap 10.

It is to be understood, however, that even though numerous characteristics and advantages of the present disclosure have been set forth in the foregoing description, together with details of the structure and function of the disclosure, the disclosure is illustrative only, and changes may be made in details, especially in matters of shape, size, and arrangement of parts within the principles of the disclosure to the full extent indicated by the broad general meaning of the terms in which the appended claims are expressed.

What is claimed is:

1. A button, comprising:
    a keycap made of transparent material, and the keycap comprising a first side surface and a second side surface opposite to the first side surface;
    four light guide blocks set on the first side surface of the keycap;
    four ultraviolet lighting elements to emit ultraviolet light, each ultraviolet lighting element set adjacent to a corresponding one of the at least one light guide block, wherein ultraviolet light emitted by the at least one ultraviolet lighting element enters into the corresponding light guide block, then is reflected by the light guide block to pass through the keycap to arrive at the second side surface of the keycap;
    wherein a depressed portion is defined in the first side surface of the keycap, the light guide blocks and the ultraviolet lighting elements are set on a bottom of the depressed portion; the keycap is generally quadrate-shaped; the four lighting elements are adhered on four corners of the bottom of the depressed portion, and each of the light guide blocks is arranged between two adjacent lighting elements.

2. The button of claim 1, wherein each of the four ultraviolet lighting elements is an ultraviolet light-emitting diode.

3. The button of claim 1, wherein each of the four light guide blocks is generally trapezoid-shaped and comprises a top surface and four side surfaces extending from sides of the top surface to connect with the first side surface of the keycap, a side surface of the light guide block adjacent to the corresponding one of the four ultraviolet lighting elements is operable to allow ultraviolet light emitted by the ultraviolet lighting element to enter the light guide block, and a height of the light guide block is gradually decreased from a first end of the light guide block adjacent to the corresponding one of the four ultraviolet lighting elements towards a second end of the light guide block.

4. The button of claim 3, wherein the sidewall at the first end of the light guide block is vertical to the first side surface of the keycap.

5. The button of claim 4, wherein a pressing bar is set on a center of the first side surface of the keycap, functioning as a triggering portion.

* * * * *